United States Patent
Archer et al.

(10) Patent No.: US 9,811,316 B2
(45) Date of Patent: Nov. 7, 2017

(54) PARALLEL, LOW-LATENCY METHOD FOR HIGH-PERFORMANCE SPECULATIVE GLOBALLY-LARGE ELEMENT EXTRACTION FROM DISTRIBUTED, SORTED ARRAYS

(75) Inventors: Charles J. Archer, Rochester, MN (US); Michael A. Blocksome, Rochester, MN (US); Joseph D. Ratterman, Rochester, MN (US); Brian Smith, Rochester, MN (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1647 days.

(21) Appl. No.: 11/758,703

(22) Filed: Jun. 6, 2007

(65) Prior Publication Data
US 2008/0307195 A1 Dec. 11, 2008

(51) Int. Cl.
G06F 7/36 (2006.01)
G06F 9/38 (2006.01)
G06F 15/80 (2006.01)
G06F 19/16 (2011.01)
G06F 9/30 (2006.01)
G06F 19/28 (2011.01)

(52) U.S. Cl.
CPC .............. *G06F 7/36* (2013.01); *G06F 9/30021* (2013.01); *G06F 9/30032* (2013.01); *G06F 9/3885* (2013.01); *G06F 15/80* (2013.01); *G06F 19/28* (2013.01); *G06F 19/16* (2013.01)

(58) Field of Classification Search
CPC .......... G06F 7/36; G06F 9/3885; G06F 15/80; G06F 19/16

USPC .............. 707/7; 708/207; 712/10, 16, 28, 30
See application file for complete search history.

(56) References Cited

U.S. PATENT DOCUMENTS

| 5,146,590 | A | 9/1992 | Lorie et al. |
| 5,307,485 | A * | 4/1994 | Bordonaro et al. ............. 707/7 |
| 5,727,200 | A | 3/1998 | Narita et al. |
| 5,857,186 | A | 1/1999 | Narita et al. |
| 5,991,785 | A | 11/1999 | Alidina et al. |
| 6,266,665 | B1 * | 7/2001 | Vaidyanathan et al. .......... 707/7 |
| 6,366,911 | B1 * | 4/2002 | Christy ............................ 707/7 |

(Continued)

OTHER PUBLICATIONS

IBM Technical Disclosure Bulletin NN9102215, Feb. 1, 1991, pp. 215-217.*

(Continued)

*Primary Examiner* — David J Huisman
(74) *Attorney, Agent, or Firm* — Cantor Colburn LLP

(57) ABSTRACT

The present invention provides a system and method for extracting elements from distributed arrays on a parallel processing system. The system includes a module that populates a result array with globally largest elements from input arrays, a module that generates a partition element, a module that counts the number of local elements greater than the partition element, and a module that determines the globally largest elements. The method for extracting elements from distributed arrays on a parallel processing system includes populating a result array with globally largest elements from input arrays, generating a partition element, counting the number of local elements greater than the partition and determining the globally largest elements.

10 Claims, 4 Drawing Sheets

(56) References Cited

U.S. PATENT DOCUMENTS 7,447,720 B2\* 11/2008 Beaumont .................... 708/207

OTHER PUBLICATIONS

Bohhari, 'Findind Maximum on an Array Processor with a Global Bus', Feb. 1984, pp. 133-139.
Dechter et al., 'Broadcast Communications and Distributed Algorithms', Jul. 1983, pp. 210-219.
Dechter et al., 'Parallel Algorithms for Multiprocessors using Broadcast Channel', Nov. 1981, 20 pages.

\* cited by examiner

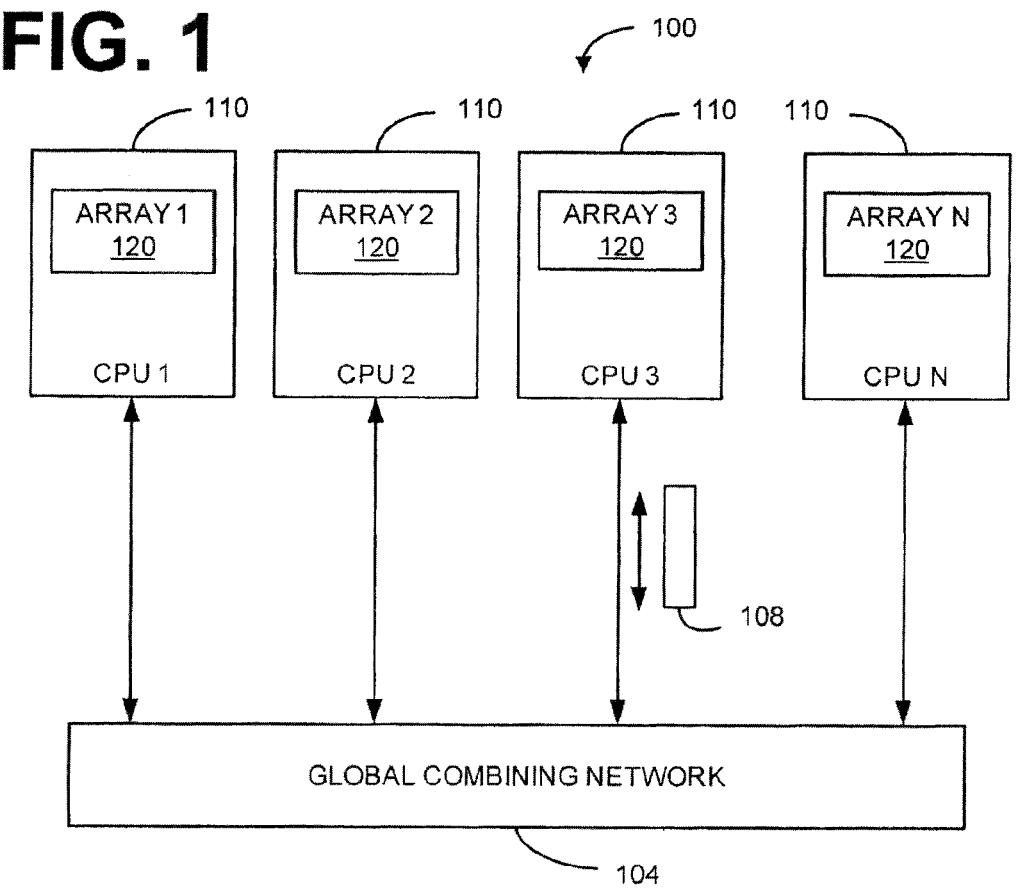

US 9,811,316 B2

PARALLEL, LOW-LATENCY METHOD FOR HIGH-PERFORMANCE SPECULATIVE GLOBALLY-LARGE ELEMENT EXTRACTION FROM DISTRIBUTED, SORTED ARRAYS

CROSS-REFERENCE TO RELATED APPLICATION

This application is related to previously pending and now abandoned U.S Patent application entitled "PARALLEL, LOW-LATENCY METHOD FOR HIGH-PERFORMANCE DETERMINISTIC ELEMENT EXTRACTION FROM DISTRIBUTED ARRAYS" filed on Jun. 5, 2007, and having Ser. No. 11/758,692, which is entirely incorporated herein by reference.

FIELD OF THE INVENTION

This invention generally relates to systems, methods, and apparatuses for array processing, and more particularly, for high-performance element extraction from distributed arrays on a parallel processing system.

DESCRIPTION OF BACKGROUND

Currently, in certain large-scale parallel applications, it is sometimes helpful to be able to find the globally largest N items out of distributed lists on P nodes.

This is particularly important in bio-informatics applications, where finding the best matches to an item is a common step in the process. These algorithms are useful in the BLAST application. There are a number of approaches to this problem, although none are particularly efficient. Applications typically do a gather operation to a root node and then a local sort/search on that node. Gather operations do not scale well and require large amounts of memory. The local sorting searching is also quite time consuming.

SUMMARY OF THE INVENTION

Embodiments of the present invention provide a system and method for extracting elements from distributed arrays on a parallel processing system. Briefly described, in architecture, one embodiment of the system, among others, can be implemented to include: a module that populates a result array with globally largest elements from the input, a module that generates a partition element, a module that counts the number of local elements greater than the partition element and a module that determines the globally largest elements.

Embodiments of the present invention can also be viewed as providing methods for extracting elements from distributed arrays on a parallel processing system. In this regard, one embodiment of such a method, among others, can be broadly summarized by the following steps: populating a result array with globally largest elements from the input, generating a partition element, counting the number of local elements greater than the partition element and determining the globally largest elements.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 is a block diagram illustrating an example configuration of a computer system utilizing the parallel, low latency methods for high-performance element extraction from distributed arrays in accordance with example embodiments of the present invention.

FIG. 2 is a block diagram example of an array of elements utilized by the computer system shown in FIG. 1.

Figure 3:
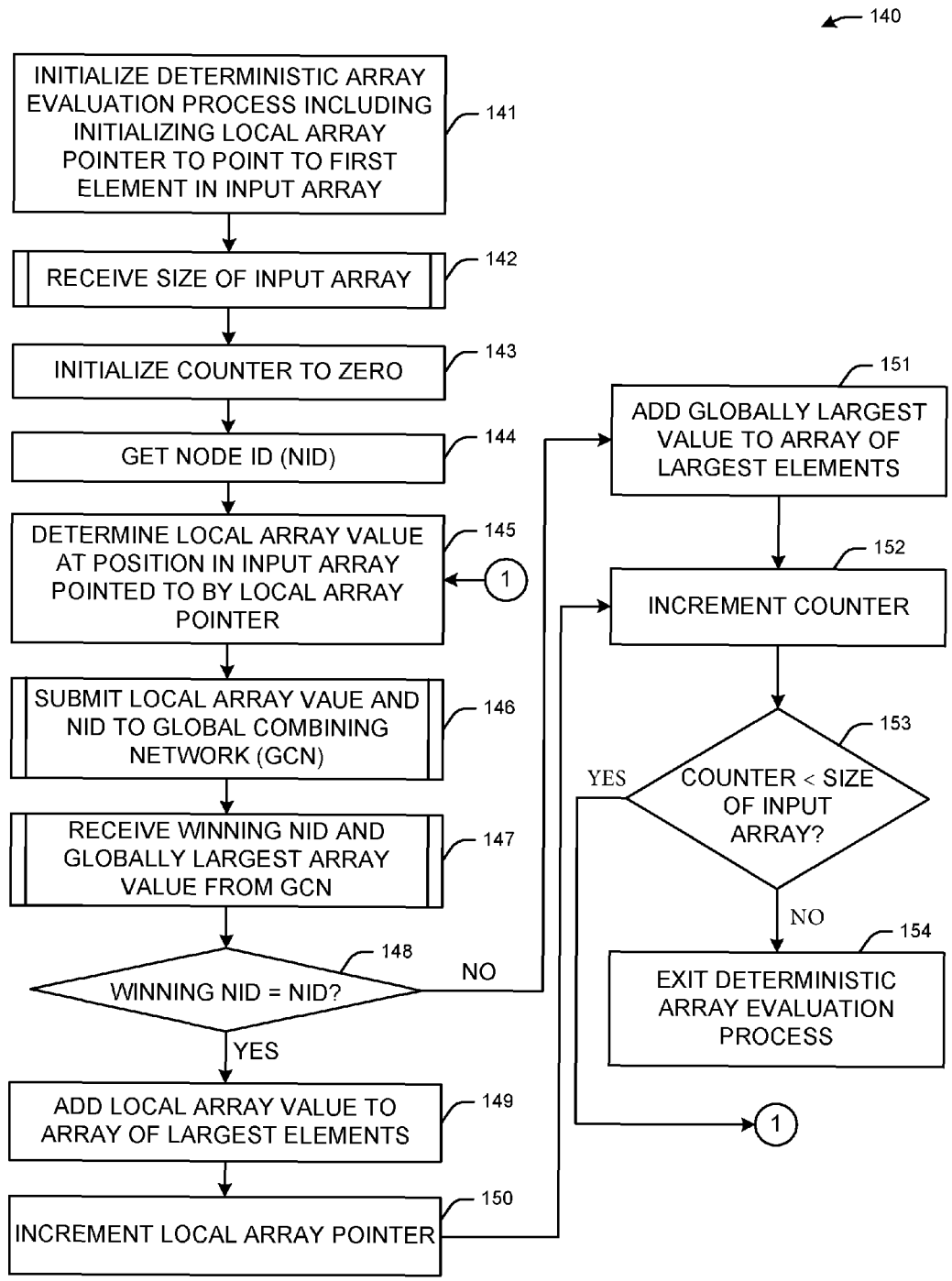
FIG. 3 is a flow chart of the deterministic array evaluation process that finds the largest global element in each iteration in accordance with example embodiments of the present invention.

The detailed description explains the preferred embodiments of the invention, together with advantages and features, by way of example with reference to the drawings.

DETAILED DESCRIPTION OF THE INVENTION

The invention addresses problems with massively parallel supercomputers. In certain large-scale parallel applications, it is sometimes helpful to be able to find the globally largest N items out of distributed lists on P nodes.

One such example where this operation of combining the globally largest N items out of the distribution list on P nodes is important is in the area of biomolecular simulations to study protein science. The life sciences are receiving special attention because the field is demonstrating explosive growth, and the life sciences are creating what will become one of the most significant industries of the new century. Indeed, with advances in bioinformatics and genomics, high-throughput screening of drug candidates, and ready access to information on the Internet, the life sciences have benefited from computational capabilities and will be driving the requirements for data, network, and computational capabilities in the future. The particular area of protein folding includes the need for determining the best docking sites for molecules and proteins. The understanding of the protein folding phenomenon is a recognized "grand challenge problem" of great interest to the life sciences.

Increased computational power translates into an increased ability to validate the models used in simulations and, with appropriate validation of these models, to probe these biological processes at the microscopic level over long time periods. A critical component of the research will be the connection of the simulations to the experimental biophysics of protein dynamic.

One such example of a massively parallel supercomputer to accomplish this is the BlueGene/L (BG/L). BG/L is a massively parallel supercomputer that contains 65536 nodes interconnected by specialized networks. The combinations of low-power chips and specialized networks have allowed BG/L to reach petaflop scale computing. Scalable parallel algorithms that utilize these networks are increasingly important.

This document defines two new methods, both which make use of a vast global combining network and this computational power. In both methods, it is assumed that the local arrays are sorted on each processor node, but there is no global order. Local arrays should be at least N elements long, so padding can be performed if necessary. In an alternative embodiment, a trivial change to the methods would remove the requirement for padding.

The two methods are a deterministic method and a speculative method. The deterministic method makes a loop N times and finds the largest global element remaining in each iteration for each position in the array. The speculative method repeatedly attempts to make an educated guess about a partitioning value. The nodes then repeatedly sum the number of elements on each node greater than the partitioning value and choose a new partitioning value, until the total number of elements greater than the partitioning value is equal to N.

FIG. 1 is a block diagram illustrating a configuration of a parallel supercomputer (i.e. a computer system) utilizing the parallel, low latency methods for high-performance element extraction from distributed arrays in accordance with example embodiments of the present invention. The configuration contains a physical machine 100 that includes central processing units (CPUs) 110 coupled via a global combining network (GCN) 104. A physical machine 100 is a parallel processing system suitable for storing and/or executing program code and can include multiple processors coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. Input/output (I/O) devices (including, but not limited to keyboards, displays, pointing devices, etc.) can be coupled to the system either directly or through intervening I/O controllers. Network adapters may also be coupled to the system 100 to enable the parallel processing system 100 to become coupled to other data processing systems or remote printers or storage devices through intervening private or public networks. Modems, cable modems, and Ethernet cards are just a few of the currently available types of network adapters.

While the present invention is not limited to any particular hardware or software platform, in an exemplary embodiment, the physical machine 100 may constitute an IBM™ BG/L (IBM and BlueGene are trademarks of IBM Corporation). GCN 104 forwards data packets 108 between the CPUs 110 on the physical machine 100. GCN 104 may be an internal network, such as one or more specialized networks, a local area network (LAN) within an organization, an external network, or combinations thereof, and may have other physical machines or devices (not shown) coupled to it.

FIG. 2 is a block diagram example of an array 120 utilized by the CPUs 110 and GCN 104 shown in FIG. 1. Each CPU 110 may utilize the high-performance distributed array element extraction methods of the present invention on the array 120. The array 120 includes a plurality of elements 121-129. In an exemplary embodiment, elements 121-129 are sorted in descending order by value. In the exemplary bio-informatics application, the element values in the array 120 indicate the best docking sites on a protein or molecule being modeled. Thus, it is sometimes helpful to be able to find the globally largest N items of the distributed arrays on multiple nodes.

This disclosure illustrates two new methods, both of which make use of a fast global combining network. These methods include the Iterative/Deterministic version and Partitioning/Speculative version. The Iterative/Deterministic version makes a loop N times, and finds the largest global element remaining in each iteration. The Partitioning/Speculative version repeatedly attempts to make an educated guess about a partitioning value. The nodes then repeatedly sum the number of elements on each node greater than the partitioning element and choose a new partitioning element, until the total number of elements greater than the partitioning element is equal to N.

In these methods, the MPI Allreduce( ) function is utilized. The MPI Allreduce( ) function can be described as a function that uses arithmetic operations to combine all values on all processors into a single value. These arithmetic operations would be done using the GCN 104. The largest value found across all arrays 120 in all CPUs 110 is then broadcast to all CPUs 110. The CPU 110 having the largest element in its array 120 then removes that element from further comparison in any subsequent operation of the MPI Allreduce( ) function.

In both cases, the methods assume that the local arrays are sorted, but there is no global order. The local arrays are at least N elements long. Padding is utilized if necessary, although a trivial algorithm change would remove a requirement for padding. If the local arrays are longer than N, one can clearly disregard the extra elements since there is no way that they could be part of the result.

For the timing discussions below, A(P) will be use to represent the time it takes to do an MPI Allreduce( ) function over P nodes. On BGL, A(P) is upper-bounded by Ln(P), with a very small constant. Other systems are able to achieve the O(Ln(P)) performance, but they generally have much larger constants which would make these approaches unreasonable.

FIG. 3 is a flow chart of a deterministic array evaluation process 140, from each CPU's perspective, which finds the largest global element in each iteration method of the present invention. Given two arrays 120 (one array 120 for input and one array 120 for output of results) and their length, the following steps populate the result array 120 with the globally largest elements from the input: loop over each element 121-129 in the result array 120; perform the Allreduce function over all nodes using the "current" element on each node, with operation MAX; and store the result in the result array 120. Whichever node contributed the largest element will advance its "current" element pointer to the next value in the input array.

The expected time for this to run is O(N*A(P)). This is clear, since the for loop will execute exactly N times, and the body of the loop will take A(P) time. More concretely, the following C/MPI code does the above for arbitrary integer arrays.

```
void biggest_N(int *narray, int *result, int size, MPI_Comm comm)
{
    int i, point=0;
    int rank;
    struct {
        int data;
        int rank;
    } work;
```

```
MPI_Comm_rank(comm, &rank);
for (i=0; i<size; ++i) {
    work.rank = rank;
    work. data = narray[point];    //" work.data" is set equal to the
                                    array value pointed to by
                                    // the local array pointer
    MPI_Allreduce(MPI_IN_PLACE, &work, 1,
    MPI_2INT, MPI_MAXLOC, comm);
    if (work .rank ==. rank)       //" work.rank" represents the node
                                    ID (NID) for the CPU and
                                    //"rank" is the winner NID
        ++point;
    result [i] = work.data;
    }
}
```

Now the code above will be described with regard to the flowchart in FIG. 3. First, the deterministic array evaluation process 140 is initialized at step 141. The initialization includes the establishment of data values for particular data structures utilized in the deterministic array evaluation process 140. For example, at step 141, a local array pointer is initialized to point to a first element in an input array 120. At step 142, a number is received indicating the size of the input array 120 (e.g., the number of elements 121-129 in the input array 120 that is to be evaluated). At step 143, a counter used to determine when the deterministic array evaluation process 140 is to be halted is initialized to zero.

At step 144, the deterministic array evaluation process 140 gets the node ID for the CPU 110. At step 145, the input array 120 is evaluated to determine the local array value at the position in the input array 120 pointed to by the local array pointer. At step 146, the deterministic array evaluation process 140 submits the local array value determined at step 145 and NID obtained at step 144 to the GCN 104. At step 147, the winning node ID (NID) and globally largest value are received from the (GCN) 104.

At step 148, a determination is made as to whether the NID for the current CPU 110 is equal to the winning NID. If it is determined at step 148 that the NID for the current CPU 110 is not the winning NID, then the deterministic array evaluation process 140 skips to step 151. At step 151, the deterministic array evaluation process 140 adds the globally largest value received at step 147 to an array of largest elements (e.g., the result array 120). However, if it is determined at step 148 that the NID for the current CPU 110 is the winning NID, then the local array value determined at step 145 is the globally largest value, and the deterministic array evaluation process 140 adds the local array value to the array of largest elements at step 149 and increments the local array pointer at step 150 to point to the next element in the array 120. From both step 150 and step 151, the deterministic array evaluation process 140 proceeds to step 152, where the counter is incremented.

At step 153, the deterministic array evaluation process 140 determines whether the counter is less than the size of the input array 120. If it is determined at step 153 that counter is less than the size of the input array 120, then the deterministic array evaluation process 140 returns to step 145 to perform a next iteration of the deterministic array evaluation process 140. However, if a positive determination is made at step 153, the deterministic array evaluation process 140 then exits at step 154.

Figure 4:
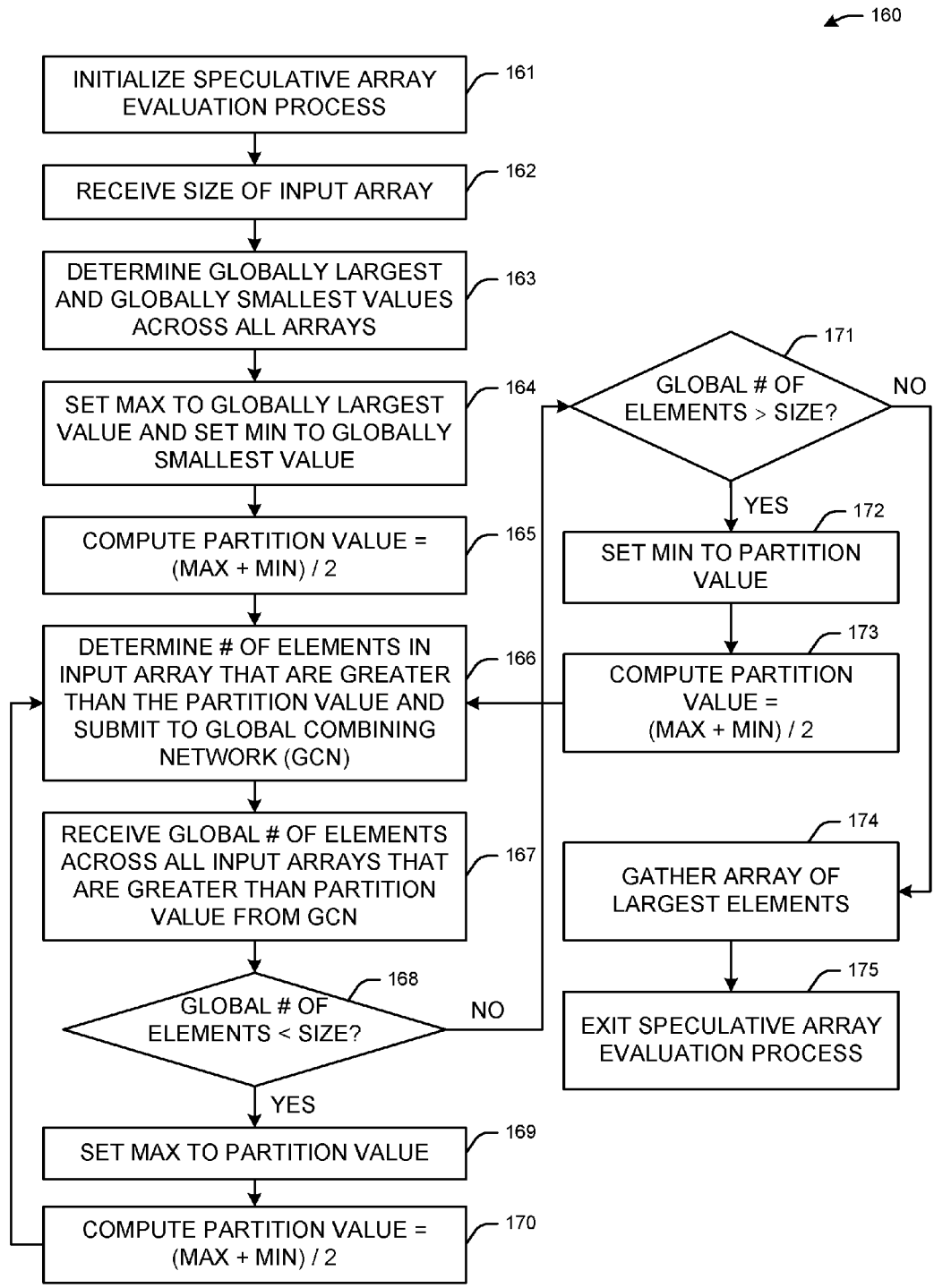
FIG. 4 is a flow chart of the speculative array evaluation process that makes an educated guess about a partitioning value in accordance with example embodiments of the present invention.

FIG. 4 is a flow chart of the speculative array evaluation process 160 that makes an educated guess about a partitioning value in accordance with example embodiments of the present invention. Given two or more input arrays and their length, the following steps populate a result output array with the globally largest elements from the input arrays: choose a partition (which has an execution time of O(A(P))); count the number of local elements greater than the partition on each local processor (which has an execution time of O(N*)); sum the local counts to find the global count (which has an execution time of O(A(P))); and while the global count doesn't equal N (which has an execution time of O(Ln(N))): choose a new partition (which has an execution time of O(1)); count the number of local elements greater than the new partition (which has an execution time of O(N*)); and sum the local count to find the global count (which has an execution time of O(A(P))).

This method is noticeably more complicated than the first. Since the loop resembles a binary search, one can expect that it will take O(Ln(N)) iterations. Choosing a partition can be done easily, so that is a simple O(1), except on the first iteration, where two Allreduces are used to calculate the bounds for an initial partition choice. Since the Allreduce used to find the sum is simple, it will be O(A(P)) each time.

The O(N*) in the description appears twice (the second in a loop), but it has a special meaning. Because the "cursor" used to count the number of local elements greater than the partition will already be indexed into the array, it will have to move less far for each successive choice of partition, as the change gets smaller and smaller. In particular, one can expect the seek distance to be cut in half with each successive choice. Alternatively, one could view it that the cursor will not have to travel further than all the way across the array. Under both ways of stating the work involved, it is clear that the sum total of work in this step is O(N). This all works out as O(A(P)+N+Ln(N)*(1+A(P)))=O(N+Ln(N)*A(P)).

More concretely, the following C/MPI code does the above for arbitrary integer arrays:

```
void biggest_N(int *narray, int *result, int size, MPI_Comm Comm)
{
    int imin, imax, sum, numprocs, point;
    double min, max, partition;
    imin imax sum = numprocs = point = 0;
    min = max = partition = 0;
    MPI_Allreduce(narray+0, &imax, 1, MPI_INT, MPI_MAX,
    Comm}; max = imax;
    MPI_Allreduce(narray+size-1, &imin, 1, MPI_INT, MPI_MIN,
    Comm}; min = imin;
    partition = (max + min ) / 2.0;
    while ( (point < size-1) && (narray[point] > partition) )
        ++point;
    while (sum != size) {
        MPI_Allreduce(&point, &sum, 1, MPI_INT, MPI_SUM,
        comm);
        if (sum != size) {
        {
            max = partition
            partition m (max + min ) / 2.0;
            while ( (point < size) && (narray[point] partition) )
                ++point;
        }
        else if (sum > size)
        {
            min = partition;
            partition = (max + min ) / 2.0;
            while ( (point > 0) && (narray(point-1) < partition) )
                --point;
        }
    }
    MPI_Comm_size (comm, &numprocs);
    int i ;
    int elements [numprocs] ;
    int displs [numprocs] ;
```

```
    MPI Allgather(&point, 1, MPI_INT, elements, 1, Comm);
    displs (0) = 0;
    for (i=1; i<numprocs; ++i)
        displs(i) = dipls[i− 1] + elements [i−1] ;
    MPI_Allgatherv(narray, point, MPI_INT, result, elements,
        displs, MPI_INT, comm)
}
```

While this second method uses a gather operation, it is gathering only the final result values which are the top N elements. Before the gather operation, each local node knows how many of the global top N elements it has. More specifically, the MPI_Allgather function may be called to obtain an array (i.e., elements), where the value at each index of the array indicates the number of elements greater than the partition value in a corresponding local input array associated with a corresponding local node. A local node may then generate an array (i.e., displs), where each index of the array represents a running count of the number of local array elements greater than the partition value. For example, the value at the second position in the displs array may indicate the number of elements greater than the partition value in a local input array associated with a first processing node, the value at the third position in the displs array may indicate the sum of the number of elements greater than the partition value in the local input array associated with the first node and the number of elements greater than the partition value in a local input array associated with a second node, and so forth. A local node can then do a gather operation if desired to consolidate the list of N largest elements to a single node.

Now the code above will be described with regard to the flowchart in FIG. 4. First, the speculative array evaluation process 160 is initialized at step 161. The initialization includes the establishment of data values for particular data structures utilized in the speculative array evaluation process 160. At step 162, a number is received indicating the number of elements 121-129 in a local input array 120 to be evaluated (e.g., the size of the local input array 120).

At step 163, the globally largest and globally smallest values across all input arrays 120 on all CPUs 110 are determined. At step 164, a first variable (hereinafter referred to as "max") is set to the globally largest value and a second variable (hereinafter referred to as "min") is set to the globally smallest value. At step 165, a partition value is computed. The partition value may be, for example, the average of the max and min. At step 166, the speculative array evaluation process 160 on the local CPU 110 determines the number of elements in the local input array 120 that are greater than the partition value computed at step 165 and submits this number to the GCN 104. At step 167, the global number of elements across all input arrays that are greater than the partition value is received from the GCN 104 (e.g., the sum of the respective number of elements in each local input array on each CPU 110 that exceed the partition value).

At step 168, a determination is made as to whether the global number of elements greater than partition value is less than the size or number of array elements to be evaluated. If it is determined at step 168 that the global number of elements is not less than the size or number of elements to be evaluated, then the speculative array evaluation process 160 proceeds to step 171. However, if it is determined at step 168 that the global number of elements is less than the size, then the max is set to the partition value at step 169, and the partition value is recomputed by averaging the max and min at step 170. The speculative array evaluation process 160 then returns to step 166 where the number of elements in the local array 120 that are greater than the partition value computed at step 170 are determined and submitted to the GCN 104.

Referring again to step 168, if a negative determination is made at step 168, the process 160 proceeds to step 171 where a determination is made as to whether the global number of elements is greater than the size or number of array elements to be evaluated. If it is determined at step 171 that the global number of elements is greater than the size, then the min is set to the partition value at step 172, and the partition value is recomputed by averaging the max and min at step 173. The speculative array evaluation process 160 then returns to step 166 where the number of elements in the local array 120 that are greater than the partition value computed at step 173 are determined.

Steps 166-175 are performed iteratively until a negative determination is made at step 171. In response to a negative determination at step 171, the speculative array evaluation process 160 proceeds to step 174 where the largest elements (e.g., the array elements in each local input array that are greater than the partition value) are gathered into a result array. The speculative array evaluation process 160 is then exited at step 175. In certain example embodiments, a median between the max and min may be computed as the partition value instead of an average.

Figure 5:
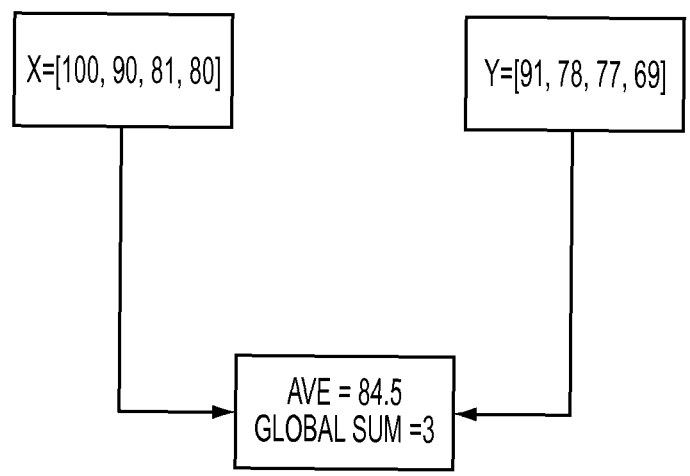
FIG. 5 is an example of the exemplary speculative array evaluation process of FIG. 4.

FIG. 5 is an example of the exemplary speculative array evaluation process of FIG. 4. The example illustrates the input array values X=[100, 90, 81, 80] and Y=[91, 78, 77, 69], in which the first average of the largest and smallest values, 100 and 69 respectively, is 84.5, and Sum=3. In this example, the speculative array evaluation process will perform three iterations. At the end of the third iteration, the max is 84.5, the min is 76.75, the partition value is 80.625 (if an average of the max and min is computed as the partition value at each iteration), and the global sum of array elements greater than the partition value is 4. The array elements greater than the partition value at the end of the speculative array evaluation process are specifically values 100, 90, and 81 from array X and value 91 from array Y.

The present invention can take the form of an entirely hardware embodiment, an entirely software embodiment or an embodiment containing both hardware and software elements. In the exemplary embodiment, the invention is implemented in software, which includes but is not limited to firmware, resident software, microcode, etc.

Furthermore, the invention can take the form of a computer program product accessible from a computer-usable or computer-readable medium providing program code or code module for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk.

Current examples of optical disks include compact disk-read only memory (CD-ROM), compact disk-read/write (CD-RAY) and DVD.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. A computer system comprising:
a plurality of processors having a local processor;
a memory operatively coupled to the local processor;
a module residing in the memory that determines a globally largest element and a globally smallest element across a set of multi-element inputs, the set of multi-element inputs comprising no duplicate elements and comprising a first multi-element input corresponding to the local processor, the first multi-element input comprising a plurality of local elements;
an assignment module residing in the memory that assigns the globally largest element to a first variable and the globally smallest element to a second variable;
a set of modules configured to perform an iterative process to determine a set of largest elements from the set of multi-element inputs, the set of modules comprising:
a size partition element generation module residing in the memory that, during a first step in the iterative process, generates a partition value from the first variable and the second variable;
a module residing in the memory that, during a second step in the iterative process, counts a number of the plurality of local elements greater than the partition value to generate a local count;
a module residing in the memory that, during a third step in the iterative process, sums the local count with one or more other local counts of elements from one or more other inputs in the set of multi-element inputs to determine a global count; and
a comparison module residing in the memory that, during a fourth step in the iterative process, determines whether the global count is greater than, less than, or equal to a size of one of the multi-element inputs,
wherein responsive to a determination that the global count is greater than the size, the assignment module assigns the partition value to the second variable and a subsequent iteration of the iterative process is performed,
wherein responsive to a determination that the global count is less than the size, the assignment module assigns the partition value to the first variable and the subsequent iteration of the iterative process is performed, or
wherein responsive to a determination that the global count equals the size, the iterative process ends;
the computer system further comprising:
a module residing in the memory that populates a distributed result array with each largest element in the set of largest elements after the iterative process ends, wherein the set of largest elements includes each element in each multi-element input that is greater than the partition value corresponding to a final iteration of the iterative process, and wherein a first element and a second element among the set of multi-element inputs that are closest to the partition value corresponding to a threshold iteration of the iterative process are not identical if a total number of elements greater than the partition value corresponding to the threshold iteration among the set of multi-element inputs is less than the size of the one of the multi-element inputs.

2. The system of claim 1, wherein the size partition element generation module generates the partition value from the first variable and the second variable by averaging a current value of the first variable with a current value of the second variable.

3. The system of claim 1, wherein the size partition element generation module generates the partition value from the first variable and the second variable by determining a median value between a current value of the first variable and a current value of the second variable.

4. The computer system of claim 1, wherein a number of largest elements in the set of largest elements equals the global count corresponding to the final iteration of the iterative process.

5. The computer system of claim 1, wherein each largest element in the set of largest elements is indicative of a respective corresponding docking site on at least one of a protein or a molecule, and wherein the computer system further comprises a module residing in the memory that selects a particular docking site as a best docking site based at least in part on a particular largest element, of the set of largest elements, corresponding to the particular docking site.

6. A method for populating a distributed result array with a set of largest elements from a set of multi-element inputs in a parallel processing system comprising a plurality of processors including a local processor, the method comprising:
determining, by the parallel processing system, a globally largest element and a globally smallest element across the set of multi-element inputs, the set of multi-element inputs comprising no duplicate elements and comprising a first multi-element input corresponding to the local processor, the first multi-element input comprising a plurality of local elements;
assigning the globally largest element to a first variable and the globally smallest element to a second variable;
performing an iterative process to determine the set of largest elements, the iterative process comprising:
generating, by the parallel processing system, a partition value from the first variable and the second variable;
counting, by the local processor, a number of the plurality of local elements greater than the partition value to generate a local count;
summing, by the parallel processing system, the local count with one or more other local counts of elements from one or more other inputs in the set of multi-element inputs to determine a global count; and
determining, by the parallel processing system, whether the global count is greater than, less than, or equal to a size of one of the multi-element inputs,
wherein responsive to a determination that the global count is greater than the size, the iterative process further comprising assigning the partition value to the second variable and performing a subsequent iteration of the iterative process, wherein responsive to a determination that the global count is less than the size, the iterative process further comprising assigning the partition value to the first variable and performing the subsequent iteration of the iterative process, or wherein responsive to a determination that the global count equals the size, the iterative process ends;

the method further comprising:

populating a distributed result array with each largest element in the set of largest elements after the iterative process ends, wherein the set of largest elements includes each element in each multi-element input that is greater than the partition value corresponding a final iteration of the iterative process, and wherein a first element and a second element among the set of multi-element inputs that are closest to the partition value corresponding to a threshold iteration of the iterative process are not identical if a total number of elements greater than the partition value corresponding to the threshold iteration among the set of multi-element inputs is less than the size of the one of the multi-element inputs.

7. The method of claim 6, wherein generating the partition value from the first variable and the second variable comprises averaging a current value of the first variable with a current value of the second variable.

8. The method of claim 6, wherein generating the partition value from the first variable and the second variable comprises determining a median value between a current value of the first variable and a current value of the second variable.

9. The method of claim 6, wherein a number of largest elements in the set of largest elements equals the global count corresponding to the final iteration of the iterative process.

10. The method of claim 6, wherein each largest element in the set of largest elements is indicative of a respective corresponding docking site on at least one of a protein or a molecule, and wherein the parallel processing system comprises a module residing in the memory that selects a particular docking site as a best docking site based at least in part on a particular largest element, of the set of largest elements, corresponding to the particular docking site.

* * * * *